United States Patent [19]

Lindner et al.

[11] Patent Number: 4,600,542

[45] Date of Patent: Jul. 15, 1986

[54] SULPHONATION PRODUCTS OF NAPHTHALENE, PROCESSES FOR THEIR PREPARATION, AND THEIR USE

[75] Inventors: Otto Lindner, Bergisch-Gladbach; Heinrich Pelster; Guido Steffan, both of Odenthal; Arnd Stüwe, Leverkusen, all of Fed. Rep. of Germany

[73] Assignee: Kramer Aktiengesellschaft, Leverkusen, Fed. Rep. of Germany

[21] Appl. No.: 232,797

[22] Filed: Feb. 9, 1981

Related U.S. Application Data

[63] Continuation of Ser. No. 96,083, Nov. 20, 1979, abandoned.

[30] Foreign Application Priority Data

Dec. 9, 1978 [DE] Fed. Rep. of Germany ....... 2853337

[51] Int. Cl.$^4$ .......................................... C07C 143/24
[52] U.S. Cl. ................................................ 260/505 C
[58] Field of Search ..................................... 260/505 C

[56] References Cited

PUBLICATIONS

Comptes Rendus (Reports), vol. 182, 1926, pp. 856–857.
Houben–Weyl, "Methoden der Organischen Chemie", vol. 9 (1955) p. 502.
Chem. Abst., vol. 75 (1971) 129027s.

*Primary Examiner*—Alan Siegel
*Attorney, Agent, or Firm*—Sprung Horn Kramer & Woods

[57] ABSTRACT

The invention concerns new sulfonation products of naphthalene, process for their preparation according to which naphthalene is sulfonated under special reaction conditions by sulfur trioxide in inert organic solvents. The new sulfonation products are used as intermediates e.g. for the production of naphthalene-1,5-disulfonic acid.

4 Claims, No Drawings

SULPHONATION PRODUCTS OF NAPHTHALENE, PROCESSES FOR THEIR PREPARATION, AND THEIR USE

This is a continuation of application Ser. No. 096,083, filed Nov. 20, 1979, now abandoned.

The invention relates to new sulphonation products of naphthalene, a process for their preparation and their use as intermediate products, for example, for the preparation of naphthalene-1,5-disulphonic acid.

It is already known to react naphthalene with $SO_3$ in inert organic solvents (s. Comptes rendus (Reports), Vol. 182, 1926, pages 856–857; Houben-Weyl "Methoden der Organischen Chemie" (Methods of organic chemistry), Vol. 9 (1955), page 502). According to Comptes rendus, 3 mol $SO_3$ are added gradually to a solution of one mol naphthalene in anhydrous chloroform. The precipitate forming during the reaction is described as an addition product of 2 mol $SO_3$ to one mol naphthalene-1,5-disulphonic acid. This addition product, upon hydrolysis, produces naphthalene-1,5-disulphonic acid in a 50% yield.

According to Houben-Weyl (loc. cit.), the solutions of 2.5 mol $SO_3$ in tetrachloroethane and 1 mol naphthalene in tetrachloroethane are added dropwise and simultaneously at 20° C. to tetrachloroethane already in the reaction vessel. Sulphonic acids are produced, which are isolated in the form of colourless particles. Concerning these sulphonic acids it is stated that, on dissolving them in water and salting them out with sodium sulphate, the sodium salt of naphthalene-1,5-disulphonic acid is produced in very pure form and in yields of 74–75%, based on naphthalene. Reproduction of this sulphonation process does however show that the yields of naphthalene-1,5-disulphonic acid do in fact amount to only 65–70%, based on the naphthalene used.

It has now surprisingly been found that by sulphonating naphthalene with $SO_3$ in inert organic solvents new naphthalene sulphonation products with considerably improved properties are obtained if naphthalene and $SO_3$ are used in a molar ratio of 1:3 to 5, preferably 1:3 to 3.6 and by mixing naphthalene and $SO_3$ in the inert solvent at temperatures of −40° to +10°, preferably −20° to 0° C., in such a way that the ratio of $SO_3$ to naphthalene during the mixing is in the range of 3 to 5, preferably 3 to 3.6 mol $SO_3$ per mol naphthalene.

The naphthalene sulphonation products obtainable under these reaction conditions produce, upon hydrolysis, naphthalene-1.5-disulphonic acid in high purity and in a yield of up to 81%, based on the naphthalene used.

As the analytical examination (IR spectra, reaction with ammonia and amines) has shown, these new naphthalene sulphonation products are oligomeric naphthalene sulphonic acid anhydrides of the formula I given below.

The invention therefore relates to new sulphonation products of napthalene of the formula

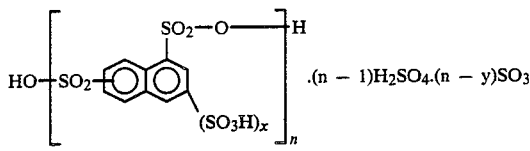

I in which n represents an integer in the range from 2 to 10, preferably 2 to 6, x denotes 0 or 1, but is 1 only in the case of at the most 10%, preferably at the most 6%, of the total sulphonated naphthalene radicals present, and y denotes 0 or an integer or fraction from 0 to 2, preferably 0 and 1.

The naphthalene sulphonic acid anhydrides of formula I, according to the invention, hold certain amounts of sulphuric acid and $SO_3$, bonded by adsorption. The amount (in mol) of sulphuric acid bonded by adsorption corresponds to the number of $-SO_2-O-SO_2-$ bridges. By treating the naphthalene sulphonic acid anhydrides with ice water this sulphuric acid is already split off, without the anhydride dissolving. The amount of $SO_3$ bonded by adsorption corresponds to the amount of $SO_3$ used which exceeds the amount of 3 mol $SO_3$ per mol naphthalene, necessary for the sulphonation of naphthalene and the formation of the anhydride bridges.

Since the naphthalene sulphonic acid anhydrides of formula I, according to the invention, contain, for the most part, units which are derived from naphthalene-1,5-disulphonic acid and naphthalene-1,5-disulphonic acid is given the common name Armstrong acid, the naphthalene sulphonic acid anhydrides according to the invention are hereinafter, for the purpose of simplicity, termed Armstrong acid anhydride or AS-AN.

The AS-AN according to the invention is, in its pure form, a very hygroscopic, flowable powder. Usually it is colourless, and often also slightly grey- or pink-coloured. In a moist atmosphere it fumes to a greater or lesser degree depending on the content of $SO_3$ bonded by adsorption. In ice water the anhydride only dissolves slowly, it dissolves more quickly on being heated or when alkali is added. AS-AN is mechanically sensitive at temperatues of above +10° C., in particular at room temperature. Under pressure and under the influence of shearing stress it is transformed, at room temperature, from a loose powder into a sticky, plastic mass.

AS-AN is thermally stable up to approx. 40° C. By heating to temperatures to 40° C. the composition of the hydrolysis products remains practically unchanged. Upon heating to higher temperatures rearrangements evidently take place. This is shown by the fact that when saponifying an AS-AN heated to temperatures higher than 40° C., the amount of naphthalenetrisulphonic acid increases particularly at the expense of naphthalene-1,6-disulphonic acid.

The AS-AN according to the invention comprises essentially oligomeric anhydrides of naphthalene-1,5-disulphonic acid. Apart from naphthalene-1,5-disulphonic acid, secondary amounts (12–18 mol %) of the other isomeric naphthalene-disulphonic acids, above all naphthalene-1,6-disulphonic acid, and secondary amounts (2–8 mol %) of naphthalene trisulphonic acid also participate in the anhydride formation.

The following is, for example, a composition typical for the naphthalene sulphonic acid anhydrides according to the invention:

Column A: Data given in percent by weight; the naphthalene sulphonic acid units substituting the anhydride are stated as free sulphonic acids, and sulphuric acid and $SO_3$, bonded by adsorption, are stated as sulphur trioxide.

Column B: Yields (in % of theory) of the naphthalene sulphonic acids constituting the anhydride, based on the napthalene used.

|   | A | B |
|---|---|---|
| Naphthalene-1,3-disulphonic acid | 0.2 | 0.3 |
| Naphthalene-1,4-disulphonic acid | 0.02 | 0.03 |
| Naphthalene-1,5-disulphonic acid | 61.0 | 80.5 |
| Naphthalene-1,6-disulphonic acid | 6.4 | 8.4 |
| Naphthalene-1,7-disulphonic acid | 2.3 | 3.0 |
| Naphthalene-1,3,5-trisulphonic acid | 2.3 | 2.4 |
| Naphthalene-1,3,6-trisulphonic acid | 4.7 | 4.9 |
| Naphthalene-1,3,7-trisulphonic acid | 0.5 | 0.5 |
| Sulphur trioxide | 22.5 | — |

In the IR spectrum the AS-AN's according to the invention exhibit the band characteristic for sulphonic acid anhydrides, at approximately 1400 cm$^{-1}$.

When reacting AS-AN with ammonia or amines, e.g. cyclohexylamine, naphthalene-1,5-disulphonic acid diamides are obtained. This amide formation can be explained only by the presence of anhydride groups. If only free sulphonic groups were present, only the formation of naphthalene sulphonic acid ammonium salts could be expected, but not the formation of naphthalene sulphonic acid amides. The water-insolubility of AS-AN, with the simultaneous dissolution of sulphuric acid, as well as the amounts of the Armstrong acid diamides and Armstrong acid amide acids formed during the AS-AN aminolysis, contradict the presence of mixed anhydrides consisting of naphthalene sulphonic acids and sulphuric acid.

The invention further relates to a process for the preparation of the naphthalene sulphonation products of formula I according to the invention. The process is characterised in that naphthalene and $SO_3$ are used in a molar ratio of 1:3 to 5, preferably 1:3 to 3.6 and naphthalene and $SO_3$ are mixed in an inert solvent at temperatures of $-40°$ to $+10°$ C., preferably $-20°$ C. to $0°$ C. in such a way that the ratio of $SO_3$ to naphthalene during the mixing is in the range of 3 to 5, preferably 3 to 3.6 mol $SO_3$ per mol naphthalene.

For the process according to the invention commercially available naphthalene and commercially available $SO_3$, prepared according to any method desired, can be used. By inert solvents those solvents are understood which are not, or practically not, acted on by $SO_3$ under the reaction conditions, and which at the same time have a sufficient dissolving power for naphthalene and $SO_3$. Particularly suitable are, for example, low-boiling chloroalkanes, i.e. those having a boiling point below 100° C., such as 1,2-dichloro ethane and 1,2-dichloro propane. Methylene chloride has proven to be particularly advantageous. Liquid sulphur dioxide is also suitable.

The quantity of solvent can vary within wide limits. In general, the solvent is used in at least such a quantity as to ensure that a well-stirrable suspension is still present after the reaction has ended. It has proven advantageous to use a total of 300 to 3000 g solvent per mol naphthalene. When using methylene chloride it has proven advantageous to use a total of 500 to 1700 g methylene chloride per mol naphthalene.

The solvent can be introduced into the reaction in varying ways. For example, the total amount of solvent to be used can be initially placed in the reaction vessel, brought to the reaction temperature and $SO_3$ can then be added in liquid or gaseous form and naphthalene in liquid form. It is also possible to initially introduce only one portion of the solvent to be used and to add either naphthalene in liquid form and $SO_3$ dissolved in the remaining solvent, or naphthalene dissolved in the remaining solvent and $SO_3$ in liquid or gaseous form. It is also possible to introduce naphthalene and $SO_3$, each dissolved in a portion of the solvent, into the remaining solvent which has already been introduced into the reaction vessel. It is further possible to use the total quantity of solvent to be used to dissolve naphthalene and $SO_3$ and to then introduce both solutions separately, preferably cooled, into the reaction vessel.

It has proven particularly advantageous to initially introduce a portion of the solvent and/or a portion of the preceding batch and to add $SO_3$ dissolved in the solvent.

It is essential in the mixing of $SO_3$ and naphthalene that the ratio of added $SO_3$ to added naphthalene is always within the range of 3 to 5. preferably 3 to 3.6 mol. This can be achieved by mixing $SO_3$ and naphthalene, preferably each in dissolved form, in a ratio of 3 to 5 mol $SO_3$ per mol naphthalene, at equal rates (simultaneous metering). It is also possible to alternately meter in small portions of $SO_3$ and small portions of naphthalene. It has proven advantageous to initially introduce a small quantity of $SO_3$ before beginning to meter in naphthalene and $SO_3$.

The reaction of $SO_3$ with naphthalene progresses very quickly under the conditions according to the invention and is generally complete a few minutes after the introduction of the components has ended. The reaction is therefore also able to be conducted continuously in a simple manner. The speed of the metering in of the components $SO_3$ and naphthalene can be selected as required, if provision is made for adequate removal of the reaction heat (approx. 500 kcal per kg naphthalene). The removal of the reaction heat can for example be achieved by wall-cooling. Removal of the reaction heat by means of boiling cooling, optionally in vacuo, is however preferred. By means of this method of procedure relatively large amounts of heat can be removed quickly and thus shorter metering-in times and higher time-space yields can be achieved. The metering-in time can be, for example, 10 to 30 minutes when using boiling cooling. Longer metering-in times are possible, they do not however, in general, provide any advantages. Preferably, after the introduction is complete, the reaction mixture is stirred for a further short period, for example 2 to 60 minutes.

In the preparation of the AS-AN according to the invention it has proven advantageous to add, immediately after the mixing of naphthalene and $SO_3$ is complete, a small amount of water, for example up to 10 g water, based on 1 mol naphthalene. By means of this addition of water, as AS-AN with a particularly low content of trisulphonated naphthalene units is obtained.

The process according to the invention can be conducted under normal pressure, elevated pressure or decreased pressure. It should merely be ensured that a sufficient amount of solvent in liquid form is always present, i.e. that in the case of boiling, for example in the removal of heat by boiling cooling, a sufficient amount of solvent remains liquid or is reliquefied by appropriate cooling. In the case of heat-removal by wall-cooling the process is preferably conducted at normal pressure. In the case of heat-removal by means of boiling cooling the pressure is advantageously set at such a level that the solvent used boils at the desired reaction temperature.

For this reason the use of those solvents is preferred which have a relatively low boiling point at normal pressure. Methylene chloride is particularly preferred as solvent, amongst other reasons, because, when it is used and when heat-removal is conducted by boiling cooling, the pressure to be used is not too low. When using methylene chloride at reaction temperatures of −5° to −10° C. and when removing the heat by boiling cooling the process can for example be conducted at pressures in the range of 80 to 150 mbar.

When the reaction has ended a suspension of the naphthaline sulphonic acid anhydride (AS-AN) in the solvent used in each case, is present. The pure, dry AS-AN can be recovered from this suspension by separating the solid contents of the suspension, e.g. by filtration, and subsequently drying them. Since the liquid phase practically no longer contains any starting compounds, the suspension can also directly be concentrated to dryness, without filtration.

The naphthalene sulphonic acid anhydride separated from the suspension, or produced when concentrating the suspension, can be freed from remains of clinging solvent by subsequent drying. The drying is preferably conducted at decreased pressure and at temperatures below 50° C. Since AS-AN is transformed into a tacky plastic mass at temperatures above −10° C. by compression and under the influence of shearing stress, at drying temperatures of above +10° C. driers are preferably used which only exert slight mechanical forces on the product, for example, tumbler driers. At drying temperatures below +10° C., in particular below 0° C., driers can also be used, without disadvantages arising, which exert greater mechanical stress on the product, e.g. driers with rotating internal fitments.

For the further processing of the AS-AN according to the invention it is in many cases not necessary to recover it in the form of a dry solid from the suspension and/or to free it from the remains of the clinging solvent. If the solvent does not hinder the further processing of the Armstrong acid anhydride, the AS-AN can be further processed both in the form of the suspension produced in the reaction and in the form of a product moist with solvent.

The AS-AN according to the invention can, for example, be used for the preparation of Armstrong acid. This preparation can be conducted by hydrolyzing the Armstrong acid anhydride with water at elevated temperature and subsequently precipitating the Armstrong acid tetrahydrate by lowering the temperature, and then isolating it and optionally washing it with sulphuric acid. The hydrolysis can, for example, be conducted at 60° to 100° C. and the precipitation of the tetrahydrate can be conducted, for example, at 5° to 30° C. In this way Armstrong acid is obtained in yields of up to 80% of theory, based on the naphthalene used for the AS-AN preparation.

Armstrong acid can be used further in varying ways, for example as a tanning agent and for the preparation of azuric acid and azurol, which are themselves important dyestuff intermediates. 1,5-diamino-naphthalene can be obtained from azurol by reaction with ammonia and 1,5-naphthalene diisocyanate can be prepared from 1,5-diamino-naphthalene by reaction with phosgene, 1,5-naphthalene diisocyanate being able to be used for the production of polyurethanes. All of these uses of Armstrong acid are known [see, for example, Ullmann's Enzyklop/ädie der Technischen Chemie (Ullmann's Encyclopaedia of Industrial Chemistry), 3rd edition (1960), Vol 12, pages 595, 605, 610 and 624; Ullmann, loc. cit., Vol. 9, pp. 1 et seq; Ullmann, loc. cit., 4th edition (1974), Vol. 8, pp. 244 et seq; Ullmann, loc. cit., Vol. 13, pp. 347 et seq; FIAT Final Report No. 1313 I, pp. 285 et seq.]

EXAMPLE 1

(a) Preparation of Armstrong acid anhydride 50 kg methylene chloride are initially introduced into a vessel made of stainless steel having a capacity of 250 l. By applying a vacuum (approx. 120 mbar) an internal vessel temperature of −5° to −10° C. is obtained. During the course of 2 hours solutions of 32 kg (400 mol) sulphur trioxide in 130 kg methylene chloride and of 16 kg (125 mol) naphthalene in 80 kg methylene chloride, both cooled to −10° C., are metered into the vessel simultaneously, in such a way that 8.5 kg of the sulphur trioxide solution and 5 kg of the naphthalene solution flow into the vessel during every five minutes. Owing the reaction heat 100 kg methylene chloride evaporate at an internal vessel temperature of approx. −7° C. The evaporating methylene chloride is condensed and is collected in a cooled receiver.

The AS-AN is precipitated as a colourless powder from the reaction mixture. The suspension formed is evaporated in an enamelled tumbler drier in vacuo at temperatures of 0° to 10° C., until dry.

47.4 kg AS-AN in the form of a colourless powder, which fumes slightly in a moist atmosphere, are obtained.

The powder exhibits the band which is characteristic of sulphonic acid anhydride at 1400 $cm^{-1}$ in the IR spectrum, in addition to the bands characteristic of free aromatic sulphonic acids.

The composition of the anhydride was determined by high-pressure liquid chromatography of a diluted, aqueous, solution, neutralised with sodium hydroxide solution, and by determining the sulphuric acid content of the aqueous solution. The following composition was determined from the analysis data:

| naphthalene-1,3-disulphonic acid | 0.2% by weight |
|---|---|
| naphthalene-1,4-disulphonic acid | 0.02% by weight |
| naphthalene-1,5-disulphonic acid | 61.0% by weight |
| naphthalene-1,6-disulphonic acid | 6.4% by weight |
| naphthalene-1,7-disulphonic acid | 2.3% by weight |
| naphthalene-1,3,5-trisulphonic acid | 2.3% by weight |
| naphthalene-1,3,6-trisulphonic acid | 4.7% by weight |
| naphthalene-1,3,7-trisulphonic acid | 0.5% by weight |
| $SO_3$ | 22.5% by weight |

(the figure given for $SO_3$ includes sulphur trioxide and the $SO_3$-content of the sulphuric acid bonded by adsorption).

(b) Saponification of the Armstrong acid anhydride into Armstrong acid

The suspension of AS-AN in methylene chloride obtained according to (a), containing 47.4 kg Armstrong acid anhydride, was metered into 33 kg of water of 60° C. already present in a 160 l steel/enamel vessel, in such a way that the temperature in the vessel was able to be kept at 70° to 75° C. Afterwards a vacuum was applied at 70° to 80° C. and the pressure was gradually lowered to 100 mbar, until the methylene chloride was completely distilled off. While stirring slowly the reaction mixture was cooled to 15° C. during the course of 6 hours. The Armstrong acid tetrahydrate was isolated from the viscous suspension obtained, by means of a peel-off centrifuge. After washing three times, each time with 5 kg of 48% strength aqueous sulphuric acid the Armstrong acid tetrahydrate was dried by centrifuging. 43 kg of Armstrong acid tetrahydrate moist with sulphuric acid (content of sulphuric acid, approx. 7.6% by weight) were obtained.

The crude product contains, in addition to 66.8% by weight of naphthalene-1,5-disulphonic acid, a further 0.33% by weight of isomeric naphthalene disulphonic acids (chiefly naphthalene-1,6-disulphonic acid) and approx. 0.1% by weight of naphthalene trisulphonic acids. The yield of pure naphthalene-1,5-disulphonic acid tetrahydrate (Armstrong acid tetrahydrate) amounts to 79.8% of theory, based on the naphthalene used.

EXAMPLES 2 AND 3

The same procedure was followed as described in Example 1, except that the sulphonation was conducted
(a) at $-20°$ C. and
(b) at 0° C.,
instead of at $-7°$ C.

The AS-AN's obtained in this way produced, upon hydrolyis, Armstrong acid tetrahydrate in
(a) in a yield of 81%, in
(b) in a yield of 78.6%,
based on the naphthalene used.

EXAMPLES 4 TO 6

256 g (2 mol) of melted naphthalene of 100° C. and
(a) 480 g (6 mol) gaseous $SO_3$
(b) 512 g (6.4 mol) gaseous $SO_3$ and
(c) 560 g (7 mol) gaseous $SO_3$
were introduced simultaneously, with good stirring, into 1,000 ml of dry methylene chloride, cooled to $-10°$ C. The introduction of the $SO_3$ lasted about one hour. The temperature of the reaction mixture was kept at $-7°$ to $-11°$ C. by means of external cooling. The reaction mixture was stirred for a further 15 minutes at 0° C. Then the deposited precipitate was filtered off rapidly on a large glass frit and dried in vacuo at 20° C. After drying, the AS-AN was obtained in all three experiments in the form of a fine powder. The yield of AS-AN was
  733 g in (a),
  761 g in (b) and
  809 g in (c).
The hydrolysis of the Armstrong acid anhydrides yielded crude naphthalene-1,5-disulphonic acids which still contained 0.3–0.6% by weight of isomeric naphthalenedisulphonic acids and 0.0–0.2% by weight of naphthalene trisulphonic acids (based in each case on pure 1,5-disulphonic acid).

The yield of pure Armstrong acid tetrahydrate was
  78.4% of theory in (a),
  79.6% of theory in (b) and
  79.1% of theory in (c),
based in each case on the naphthalene used.

EXAMPLE 7

256 g (2 mol) of melted naphthalene of 100° C. and 536 g (6.7 mol) of liquid sulphur trioxide of 40° C. were simultaneously added dropwise, at $-25°$ C., under external cooling and with good stirring, during the course of 2 hours, to 1,000 ml of dry 1,2-dichloro ethane, the addition being conducted in such a way that both compounds had been completely metered in by the same point in time and that the ratio in which they were metered in remained the same for the total metering-in period. Stirring was continued for 1 hour at $-10°$ C. and 30 minutes at 0° C. Then the pulverulent precipitate was filtered off.

The pulverulent AS-AN, moist with solvent, obtained in this way was dissolved in 755 ml water and the aqueous solution was separated from the 1,2-dichloroethane which precipitated out. The aqueous solution was heated to 70° C., mixed, at 70° to 80° C., with 290 g of 100% strength sulphuric acid and then cooled to $+10°$ C. while stirring. The Armstrong acid tetrahydrate which crystallized out during cooling was filtered off on a frit and washed three times, each time with 50 ml of 50% strength sulphuric acid cooled to $+10°$ C. 895 g Armstrong acid tetrahydrate moist with sulphuric acid were obtained.

The content of Armstrong acid in the product moist with sulphuric acid (according to high pressure liquid chromatography and elementary analysis): 455 g ($=79\%$ of theory, based on the naphthalene used).

When, instead of 1,000 ml of dry 1,2-dichloro ethane, the same amount of dry 1,2-dichloro propane was used, the yield of Armstrong acid was 78.6%, based on naphthalene used.

EXAMPLE 8

The sulphonation of naphthalene with sulphur trioxide was conducted as described in Example 1(a). After the addition of sulphur trioxide and naphthalene was complete, the reaction mixture was stirred for a further 10 minutes at $-7°$ to $-8°$ C. Then, during the course of 15 minutes, 0.9 kg of water was introduced (via jets) in finely-divided form into the Armstrong acid anhydride suspension, at $-7°$ to $-5°$ C. and with rapid stirring. The reaction mixture mixed with water was stirred for a further 30 minutes. Then the precipitated reaction product was filtered off on a pressure filter and after briefly blowing nitrogen over the product, the latter was dried in a vacuum drying cabinet at 20° to 25° C. and a pressure of 400 to 25 mbar.

48.7 kg AS-AN, in the form of a pale grey amorphous powder, were obtained.

The hydrolysis of the Armstrong acid anhydride produced a crude Armstrong acid tetrahydrate, which contained 0.2% by weight of isomeric naphthalene disulphonic acids and 0.05% by weight of naphthalene-1,3,5-trisulphonic acid. The yield of pure Armstrong acid tetrahydrate was 80.5% of theory, based on the naphthalene used.

We claim:

1. A process for the preparation of sulfonation products of naphthalene by reacting naphthalene with $SO_3$ in the presence of methylene chloride, wherein naphthalene and $SO_3$ are brought together in the methylene chloride at temperatures of $-40°$ to $+10°$ C., in such a way that the ratio of $SO_3$ to naphthalene during the mixing is in the range of 3 to 5 mol $SO_3$ per mol naphthalene.

2. The process of claim 1, wherein the ratio of $SO_3$ to naphthalene during the mixing is in the range of 3 to 3.6 mol of $SO_3$ per mol of naphthalene.

3. The process of claim 1, wherein the reaction is conducted at $-20°$ to 0° C.

4. The process of claim 1, wherein after the addition of naphthalene and $SO_3$ has ended a small amount of water is added.

* * * * *